United States Patent [19]

Wernli et al.

[11] 4,248,741

[45] Feb. 3, 1981

[54] METHOD OF MAKING CATALYSTS FOR THE PRODUCTION OF ETHYLENE OXIDE

[75] Inventors: Walter L. Wernli; William E. Fry, both of Angleton; Steve F. Janda, Brazoria, all of Tex.

[73] Assignee: The Dow Chemical Company, Midland, Mich.

[21] Appl. No.: 43,414

[22] Filed: May 29, 1979

[51] Int. Cl.³ .................. B01J 21/04; B01J 23/02; B01J 23/50

[52] U.S. Cl. .................. 252/463; 260/348.34

[58] Field of Search .................. 252/463, 476; 260/348.34

[56] References Cited

U.S. PATENT DOCUMENTS

| | | | |
|---|---|---|---|
| 3,423,328 | 1/1969 | Keith et al. | 252/463 X |
| 3,575,888 | 4/1971 | Long | 252/476 |
| 3,702,259 | 11/1972 | Nielsen | 252/463 X |
| 3,887,491 | 6/1975 | Ramirez et al. | 252/476 X |
| 4,039,561 | 8/1977 | Mitsuhata et al. | 252/463 X |
| 4,102,820 | 7/1978 | Cavitt | 252/476 X |
| 4,123,385 | 10/1978 | Rebsdat et al. | 252/463 X |

*Primary Examiner*—W. J. Shine
*Attorney, Agent, or Firm*—A. C. Ancona

[57] ABSTRACT

An improved process for preparing a silver catalyst which comprises impregnating a porous alumina support with a silver salt, preferably silver nitrate, by contacting a quantity of the support with an aqueous solution of the salt in sufficient amount to be completely absorbed by said support while under a vacuum. A dispersing agent is also employed in the aqueous silver salt solution. The support is dried by heating, e.g. 100° C., under vacuum and then, while still under vacuum, impregnated with a reducing agent employing an amount sufficient to be completely absorbed by the support. Subsequent heating at a higher temperature, e.g. 250° C., reduces the silver salt to silver metal. A catalyst is produced which, when employed for the oxidation of ethylene, permits the process to run 5°–10° C. cooler at the normal conversion and also gives an improved yield.

4 Claims, No Drawings

METHOD OF MAKING CATALYSTS FOR THE PRODUCTION OF ETHYLENE OXIDE

BACKGROUND OF THE INVENTION

This invention relates to a novel method of preparing a silver catalyst and its use in the process of making ethylene oxide by the partial oxidation of ethylene in the vapor phase. Silver-containing catalysts in which the catalytically active component is the metal itself are well known in the art. An important use for the catalyst is in the direct oxidation conversion of alkenes to the corresponding vicinal epoxides, particularly in preparing ethylene oxide from ethylene by reacting ethylene with oxygen in the vapor phase.

Methods known to the art for making such catalysts include soaking a carrier or support in aqueous solutions of silver salts to impregnate it. Thereafter the thus-impregnated salts are reduced to silver metal prior to utilization in the process for oxidizing ethylene. Reduction is normally accomplished by heating in the presence of a reducing agent or by thermal decomposition of the salt. This is done at temperatures within the range of 125° C. to 400° C. and preferably from 200° C. to 300° C. Alternatively, the silver salt may be deposited from a slurry. Either slurry or solution also may contain a reducing agent, or the reducing agent may be subsequently applied.

The commonly used reducing agents are organic compounds which include polyhydric alcohols, such as liquid glycols (e.g. ethylene, propylene, and butylene glycols), glycerol, aqueous sugar solutions, aqueous polyvinyl alcohol solutions, the polyglycols, (e.g. polyethylene and polypropylene glycols) preferably of relatively low molecular weight; also included are aqueous solutions of such polyglycols, the water soluble glycol alkyl ethers, and the like. Other excellent reducing agents are high-boiling esters of carboxylic acids such as diethyl sebacate, dibutyl sebacate, dioctyl sebacate, dicapryl sebacate, diethyl phthalate dibutyl phthalate, dibutyl azelate, dioctyl azelate and dicapryl azelate.

One of the criteria for commercially useful silver catalysts is that the silver be finely divided and relatively homogeneously dispersed on the catalyst support. Dispersing agents are advantageously used in order to obtain such silver deposits, especially suitable as dispersing agents are organic amines such as ethylene diamine and ethanolamine and others disclosed in U.S. Pat. No. 3,702,259; and those naturally occurring gums such as disclosed in U.S. Pat. No. 3,887,491. These natural gums are, for example, karaya, ghatti, and tragacanth, which are plant exudates; root or seed extracts, such as guar, saponin and locust bean, psyllium seed, and quince seed. Seaweed extracts such as agar, carrageenin and furcellaran are also useful as well as others such as gelatin, casein, and pectin. Certain chemically modified derivatives of starch, of cellulose and poly sacharides (the unmodified forms of which are insoluble) are also included as substances classifiable as gums and are useful as dispersing agents in the preparation of catalysts.

While aqueous solutions are usually satisfactory to use in dissolving the dispersing agents, those which are less water soluble may be soluble in one of the aliphatic alcohols having from 1 to 4 carbon atoms, or may be soluble in mixtures of alcohol with water. Mixtures of an alcohol with water are particularly useful if the silver salt which is being employed is not sufficiently soluble in the alcohol alone. Representative silver salts which may be employed are silver salts of certain inorganic acids for example, silver nitrate, silver chlorate, and silver metaborate, or salts of carboxylic acids such as silver acetate, silver propionate and silver formate may be used. The preferred salt is silver nitrate because it is so readily soluble and easily reduced, either thermally or with an organic reducing agent or hydrogen.

Supports known to be useful for making silver catalysts are for example alumina, zirconia, corundum, mullite, silicon carbide and carbon. Alumina is preferred and especially a porous alumina of low surface area, i.e. less than one square meter per gram.

While silver is the metal most useful from a commercial standpoint in providing the catalytic effect necessary to obtain ethylene oxide, most commercial catalysts additionally contain small amounts of a promoter. The amount employed is usually from a few parts per million up to one or two percent, based on the weight of the total catalyst. Representative promoters include the alkali and alkaline earth metals which are usually present as their oxides. Thus lithium, sodium, potassium, rubidium, cesium, calcium, barium, cadmium, and the like, are added as their salts to the solution of the silver salt which is applied to the support and on subsequent heating are converted to their oxides.

Other ways known to the art of adding the promoter compound are to add it to the support prior to or subsequent to the application of the silver salt. In each case the particular salt applied is dried prior to applying the solution of the second salt. Generally the promoters, when applied first, are converted to their oxides and the silver salt when applied first, is reduced to silver. To insure adequate penetration of the pores of the support, a vacuum is applied when applying the aqueous solutions of the silver salt or of the promoter salt. This is described in U.S. Pat. No. 3,575,888.

An example of a procedure for preparing a good catalyst of the prior art is to soak an alumina support in an excess of an aqueous solution containing the silver nitrate and barium nitrate as a promoter along with a dispersing agent, such as saponin, soaking for a period of time and following that with a period of draining in order to remove excess liquid. The wetted support is then dried at atmospheric pressure, or under reduced pressure, or under a flow of nitrogen for a period of time sufficient to dry the support. The burdened, dried support is then reduced by immersing it in a bath of high-boiling mineral oil containing a small amount of a reducing agent such as the high-boiling esters previously mentioned. Although a high-boiling ester can be used neat, it is preferred to use the ester at a rate of about 10% in the mineral oil for economic considerations. Either way, once the reduction is complete the excess oil and or high-boiling ester must be drained off and any remaining on the catalyst support needs to be vaporized or burned off by heating.

According to the present invention, using a modification of the previously described process which is representative of a good process known in the prior art a catalyst has been prepared which gives excellent conversions equivalent to those known to the prior art, and better yields, but does so at a process temperature which is 5 to 10 degrees lower than normally expected to provide a saving in energy and potentially a longer useful life.

SUMMARY OF THE INVENTION

The present invention is an improved process for preparing silver catalysts useful in production of ethylene oxide which comprises impregnating a catalyst support with an aqueous solution of a silver compound by employing a vacuum to insure penetration of substantially all of the pores of the support; drying the thus impregnated support with heat and vacuum; applying a reducing agent, usually with heat, to the support while under vacuum so as to assure complete penetration of the pores of the support. Following this the so-impregnated support is placed in an oven maintained at a temperature within the range of 200° to 500° C. for a period of time sufficient to accomplish the reduction of the silver compound to silver metal to form the finished catalyst.

DETAILED DESCRIPTION OF THE INVENTION

In a representative operation an aqueous solution containing 54.8% silver nitrate, and 0.38% barium nitrate was used to impregnate a catalyst support consisting of 3/16" diameter spherical porous alumina pellets having a surface area less than 1 m$^2$/g. The amount of solution used was an amount sufficient to completely wet the catalyst without any appreciable excess of solution. A vacuum was then applied at ambient temperature for 30 minutes and drying was accomplished by heating to a temperature of 100° C. while maintaining that vacuum. The dry impregnated support, while still under vacuum, was then contacted with a high-boiling ester, in this case dioctyl sebacate, which was heated to a temperature of about 100° C. to allow penetration of all the pores by the reducing agent. When all of the reducing agent had been absorbed, the support was then placed into a kiln heated to a temperature of 400° C. for a sufficient time to reduce the silver salt. The silver and barium on the support were determined to be about 10% and 180 ppm, respectively. The entire process was then repeated in order to obtain a catalyst containing a greater amount of silver. After the second processing the catalyst contained 17.9% silver and 360 ppm barium.

The solutions from which the catalytic salts are applied are aqueous solutions containing generally from 15% up to 80% by weight of silver nitrate and from 0.01 to 0.7% by weight of the barium nitrate. The dispersing agent, preferably the naturally occurring gums, is used in an amount of from about 0.5% to 15.0% by weight of the solution. The solution is of sufficient concentration to provide from 12 to 23% silver on the finished catalyst and from 100 to 1,000 parts per million of barium. The temperature of drying the support after application of the silver and promoter salts is from about 50° C. to about 150° C., preferably from about 75° C. to about 125° C. Since the high-boiling esters (i.e having boiling points above 300° C.) are very viscous at room temperature, heat and vacuum must be applied in order to penetrate the small pores of the catalyst support so as to allow complete reduction of all of the silver salts on the support. Heat is applied to obtain a temperature in the same range as for the preceding drying step, i.e. 50° C.-150° C. The vacuum employed for the impregnation of the silver salt, the drying step and the application of the reducing agent is essentially the same and within the range of 20"-30" Hg. The reduction itself is conducted at temperatures within the range of 150° C. to 300° C., but preferably at from 180° C. to 250° C.

EXAMPLE I

A high purity porous alumina (99.5+% Al$_2$O$_3$) support, having a surface area of <1 m$^2$/g, in the form of 3/16" spheres was impregnated with a silver salt by (a) contacting 1050 lbs. of the support with 340 lbs. of an aqueous solution (54.8% AgNO$_3$, 0.38% Ba(NO$_3$)$_2$ together with 27.0 lbs. of an aqueous solution containing 5% photogel and 6% gum arabic as dispersing agents, in a rotary drum under a vacuum of 29" Hg. After the solution was completely absorbed, the support was heated while under vacuum at a temperature of 100° C. for four hours. Then 200 lbs. of dioctyl sebacate (DOS) was added to the support while still under vacuum at the 100° C. temperature. After the DOS was completely absorbed, the support was loaded into a kiln heated to a temperature of about 400° C. to accomplish the reduction of the impregnated salt to silver metal; (b) after cooling to room temperature, the catalyst was sent through the same procedure, applying a second coating of silver to the first by employing 325 lbs. of the same salt solution and 26.0 lbs. of the same dispersant solution. Reduction was accomplished with the same amount of DOS. The finished catalyst contained 17.9% Ag and 360 ppm Ba.

Comparative Example

The same type alumina support as that used in Example I was contacted with an aqueous solution containing 54.8% silver nitrate, 0.38% barium nitrate, and an aqueous dispersant solution containing 5% photogel and 6% gum arabic. A weight of 1050 lbs. of the carrier, 340 lbs of the salt solution and 24.5 lbs of the dispersant solution were contacted under a vacuum in a rotary drum. The support completely absorbed the solution and was then dried by heating at a temperature of 100° C. for four hours. Reduction of the dried impregnated support was accomplished by immersing in a bath of mineral oil containing 5% DOS reducing agent at 200° C.–250° C. After reduction the catalyst was loaded into a kiln heated at 400° C. to remove the excess oil. This procedure was then repeated to obtain a catalyst containing 17.5% Ag, substantially the same amount of silver as that of Example I, and 360 ppm Ba.

EXAMPLE II (Use of the catalyst of the invention)

Catalyst made according to the manner of Example I and containing 17.9% silver, 360 ppm barium was employed in a commercial operation.

The feed gas to the reactor contained, by volume, about 4–5% ethylene, 7–8% CO$_2$ and 5.5–6.5% oxygen, the balance being nitrogen, argon and water vapor. Temperature conditions were maintained so as to effect a conversion of about 31% of the ethylene. Eighteen readings were taken over a period of thirty days. Readings were taken on the 1st, 4th, 5th, 7th, 9th and 11th days, and on the 13th through the 17th days and on the 19th, 21st, 23rd, 25th, 27th, 29th, and 30th day. The average yield of ethylene oxide during that period was 72.6%. The average temperature required for a 30.9% conversion was 256° C.

Comparative Run: (Use of the comparative catalyst)

A catalyst prepared according to the Comparative Example and containing the same amount of silver and barium was placed in a like commercial reactor and run over the same identical period of time, readings being taken on the same days. At the end of the 30-day period, during which time the eighteen readings were taken, the average yield of ethylene oxide was 70.9%. The average temperature required for the 31.1% conversion of ethylene to obtain this yield was found to be 264° C.

From the above comparative data, it is seen that the process of the present invention allows for an improvement in yield at the same conversion and, concurrently therewith, approximately 8° C. temperature advantage. Thus, the catalyst made by the process of the invention requires less energy to obtain the same conversion and a better yield. Additionally, catalysts which perform at lower temperatures ordinarily have a longer useful life.

We claim:

1. A process for making an improved silver catalyst for use in producing ethylene oxide by reacting ethylene with oxygen in the vapor phase at an elevated temperature in the presence of said catalyst, which comprises,
    (1) Impregnating a porous alumina support by
        (a) contacting said support with an aqueous solution of a silver salt, and a barium salt as promoter while
        (b) evacuating to insure substantially complete penetration of said porous support.
    (2) Drying said impregnated support by heating under vacuum.
    (3) Impregnating said dry support with a reducing agent by,
        (a) contacting said support with a reducing agent while under
        (b) vacuum to insure substantially complete penetration of said porous support, and
    (4) Heating said support to reduce said silver salt on said support to silver metal.

2. The process of claim 1 wherein the silver and barium salts are silver nitrate and barium nitrate.

3. The process of claim 1 or 2 wherein the reducing agent is an organic ester selected from the group of esters consisting of diethyl phthalate, dibutyl phthalate, diethyl sebacate, dibutyl sebacate, dioctyl sebacate, dicapryl sebacate, dibutyl azelate, dioctyl azelate and dicapryl azelate.

4. The process of claim 1 wherein the vacuum employed in steps 1(b), 2, and 3(b) is within the range of about 20" Hg to about 30" Hg.

* * * * *

UNITED STATES PATENT AND TRADEMARK OFFICE
CERTIFICATE OF CORRECTION

PATENT NO. : 4,248,741
DATED : February 3, 1981
INVENTOR(S) : W. L. Wernli, et al It is certified that error appears in the above-identified patent and that said Letters Patent are hereby corrected as shown below:

Column 1, line 41, after azelate add --and the like.-- .

Signed and Sealed this

Fourteenth Day of July 1981

[SEAL]

Attest:

GERALD J. MOSSINGHOFF

Attesting Officer     Commissioner of Patents and Trademarks